United States Patent
Koerner

[11] Patent Number: 5,785,048
[45] Date of Patent: Jul. 28, 1998

[54] INHALER DEVICE WITH MEANS FOR ASSESSING ITS DEPLETION LEVEL

[76] Inventor: Steve J. Koerner, 2313 N. Sinagua Cir., Mesa, Ariz. 85203

[21] Appl. No.: 699,162

[22] Filed: Aug. 16, 1996

[51] Int. Cl.$^6$ .............................................. A61M 11/00
[52] U.S. Cl. .................. 128/200.23; 128/205.23; 116/215; 116/227
[58] Field of Search .................. 128/200.23, 200.14, 128/205.23; 222/41, 402.1; 239/71, 73, 74, 338; 73/149, 290 R; 116/215, 227, 327, 328

[56] References Cited

U.S. PATENT DOCUMENTS

| | | | |
|---|---|---|---|
| 2,707,930 | 5/1955 | Miles | 116/114 |
| 2,715,337 | 8/1955 | Wilson et al. | 73/290 |
| 3,487,886 | 1/1970 | Sunnen | 288/243 |
| 3,994,421 | 11/1976 | Hansen | 222/182 |
| 4,350,265 | 9/1982 | Griffiths et al. | 222/38 |
| 4,384,629 | 5/1983 | Kotzin | 177/224 |
| 4,565,302 | 1/1986 | Pfeiffer et al. | 222/38 |
| 4,637,528 | 1/1987 | Wachinski et al. | 222/182 |
| 4,817,822 | 4/1989 | Rand | 222/38 |
| 4,876,891 | 10/1989 | Felt et al. | 73/426 |
| 4,961,472 | 10/1990 | Pratt | 177/216 |
| 4,989,334 | 2/1991 | DuBose | 116/215 |
| 5,020,527 | 6/1991 | Dessertine | 128/200 |
| 5,125,466 | 6/1992 | Felt et al. | 177/207 |
| 5,284,133 | 2/1994 | Burns et al. | 128/200.23 |
| 5,319,162 | 6/1994 | Ness | 177/231 |
| 5,349,945 | 9/1994 | Wass et al. | 128/200 |
| 5,392,768 | 2/1995 | Johansson et al. | 128/200.23 |

Primary Examiner—Aaron J. Lewis
Assistant Examiner—William J. Deane, Jr.
Attorney, Agent, or Firm—Cahill, Sutton & Thomas P.L.C.

[57] ABSTRACT

A balance mechanism incorporates the housing of an aerosol delivery device which accepts and supports a cylindrical medicament cartridge. An unstable balance mechanism produces a definitive toggling action between mechanical states at the specified depletion level at which reliable dosage metering is no longer assured. In one embodiment, a fulcrum structure is formed in one side of an inhaler housing that causes the housing and the cartridge to pivot or rotate about an axis to indicate the depletion of the useful mass of the contents of the cartridge. In this embodiment, the rotation of the housing and cylindrical container is about the pivot axis located at the apex of the fulcrum formed in the housing when the housing is supported on a horizontal surface. The mechanism can also utilize the known mass of an associated mouthpiece cover or other bias weight to modify the balance criterion so as to assess whether the vessel contains a minimum reserve quantity of medicament above and beyond the reliable dosage metering level. A stable balance mechanism may additionally or alternatively be incorporated in the housing of the inhaler for assessing the continuous state of depletion of the aerosol vessel ranging from completely full to completely empty. The stable balance mechanism incorporates a pivoting needle that indicates an analog estimate of the depletion level.

17 Claims, 3 Drawing Sheets

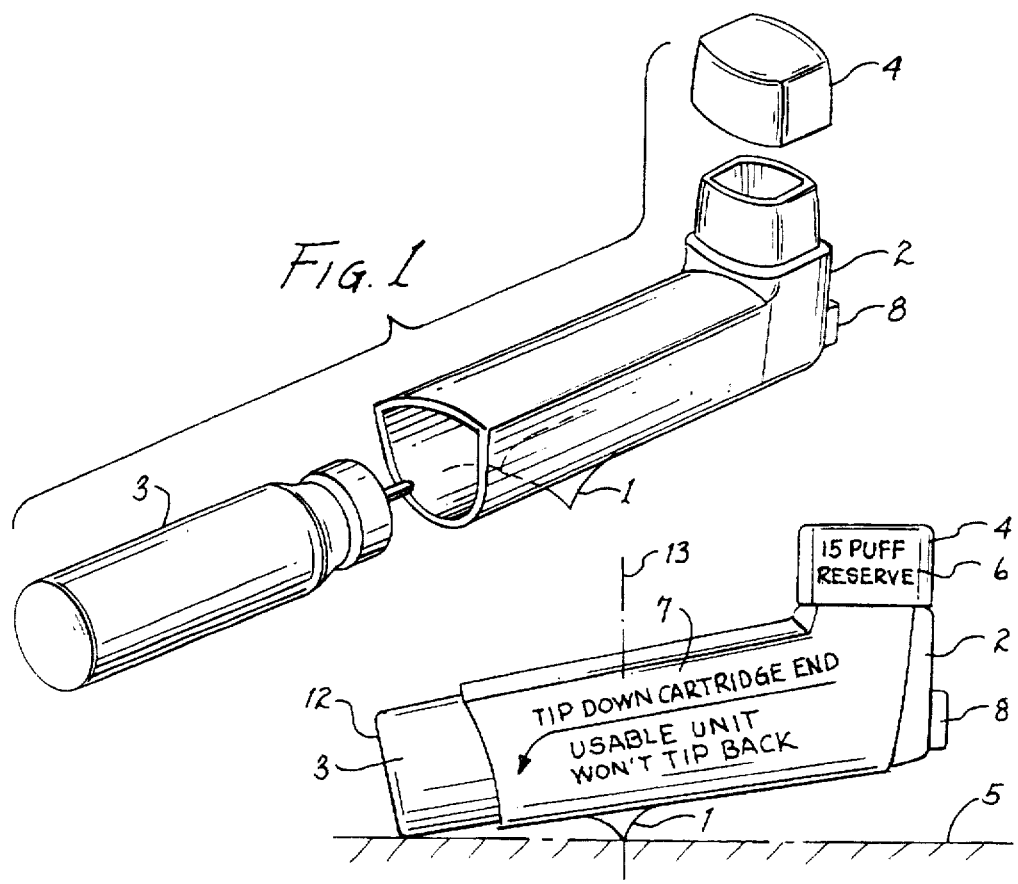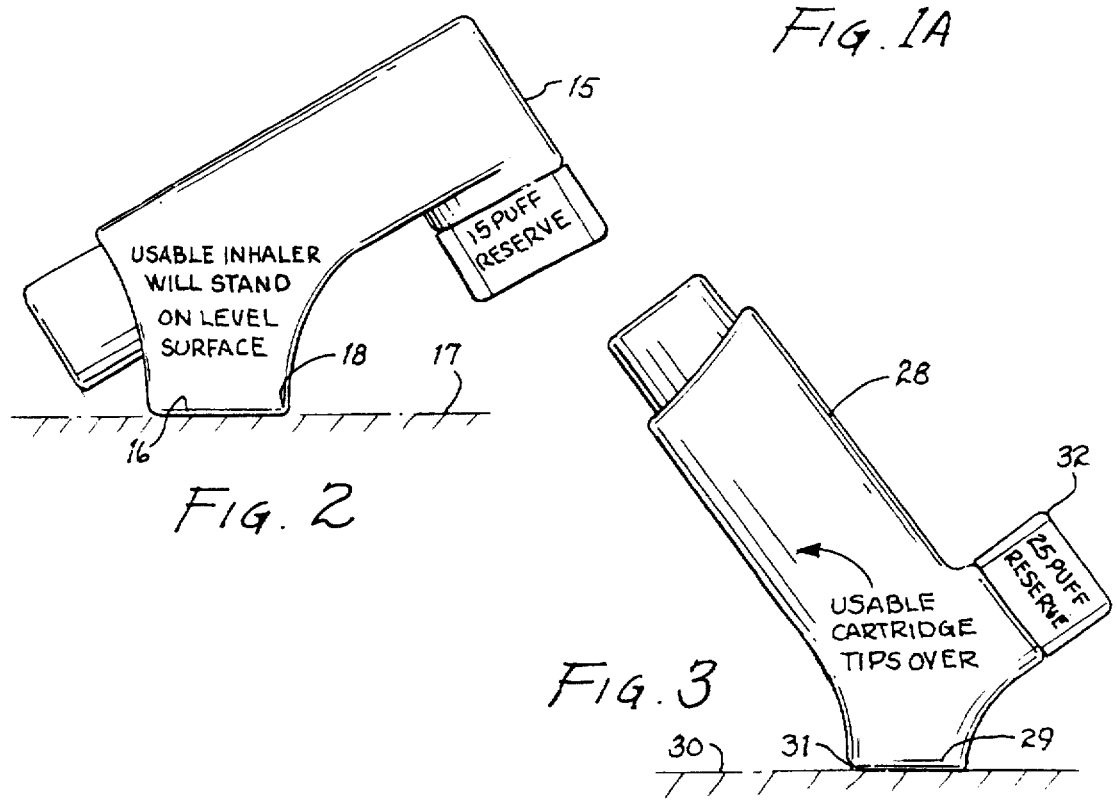

INHALER DEVICE WITH MEANS FOR ASSESSING ITS DEPLETION LEVEL

BACKGROUND OF THE INVENTION

The present invention relates to devices for dispensing medicaments from pressurized containers, and more particularly, to such devices incorporating a means for permitting the continuous determination of the amount of medicament remaining in the container.

Aerosol medicaments are commonly dispensed in opaque pressurized cartridges which do not provide a convenient mechanism for assessing the amount of their content. In normal practice these vessels are inserted in a hand-held dispensing device sometimes referred to as an adapter. The adapters are commonly positioned in or near the patient's nose or mouth and, when actuated, dispense a controlled quantity of medicament which is destined for the nasal cavities, bronchioles or lungs of the patient.

A significant problem with these inhaler devices is related to the difficulty patients have in assessing when the inhalers are functionally depleted. A functionally depleted inhaler canister normally has a remaining mass of material which is not intended to be accessed since the metering of the drug becomes inaccurate and unreliable below a particular level. In the prior art, there are no accurate and convenient methods that a user can apply to make that assessment. The prior art generally incorporates one of five techniques that a patient may use to attempt to make such assessment.

In the first prior art technique, each actuation of the inhaler can be counted and logged. This is inconvenient due to the necessity of performing protracted and precise record keeping. If any actuations or test firings are not properly accounted for, the consequence is unsafe usage beyond the end of the canister's life. Few patients use this method despite the fact that the drug manufacturers normally express the capacity of their cartridges in terms of the number of available actuations. Counting actuations is, in fact, an indirect method of estimating remaining capacity. Counting will not yield a satisfactory estimate of remaining capacity unless the initial load is precisely controlled and the metering rate is precisely controlled. If, for example, a patient uses an inhaler device in a predominantly warm or cold environment, he may not get a correct result from counting due to the temperature effect on the metering rate.

The second prior art technique that is commonly advocated by medical professionals is to periodically remove the cartridge from the adapter and place it in a pan of water. An indication of the amount of medicine remaining in the cartridge is effected by observation of how the canister floats in the water. This technique is cumbersome and quite imprecise.

The third prior art technique, used by patients who use inhalers on a regular schedule, the number of actuations used per day may be divided into the capacity of the cartridge to calculate and project to the last day of safe usage. The problem with this technique is that the medications are often used to treat disease conditions, such as asthma, which are variable in nature; only a small portion of patients use the inhalers with such precise regularity that the date projection method could be relied upon. Like the counting method identified above, this technique yields an indirect estimate of usage which may not be accurate under all conditions.

The fourth prior art technique is to directly weigh the inhaler cartridge. This method has the potential to be accurate but the difficulty is that few patients have access to the expensive scale that is needed to make an accurate measurement. Also, drug manufacturers typically do not promulgate useful data as to the exact weight of the cartridges in the various states of depletion.

The fifth and most commonly practiced prior art technique used by patients is to shake the inhaler along its longitudinal axis in order to detect the lagging inertia of the fluid content. Although this technique is convenient, it is very inaccurate. Estimating mass by such a qualitative sensory perception is not reliable and the patient has no way to calibrate such an experimental process.

A large portion of the population of users do not fully recognize the important distinction between the fully depleted and the functionally depleted state of the inhaler. As a result many, if not most, patients attempt to continue using their cartridges well beyond the point at which the dosage metering becomes unreliable.

Normally, the pressurized metered dose type inhalers, for example, will continue to produce a puffing action when actuated well after the point at which the cartridge is functionally depleted. Beyond this point, the dosing rate is unreliable and often greatly diminished as compared to a fresh cartridge. Yet, the patient has no practical way of recognizing the diminished output of the device. This problem has been recognized by medical researchers and reported in various journals. Asthmatic patients have frequently been found to have depleted the medicant without knowing of the depletion with the resulting risks. Medical investigators have determined that unknowingly running out of medication may provoke rebound bronchospasm and increase the risk of morbidity and even mortality. These investigators concluded that aerosol metered dose inhalers give insufficient information about the drug remaining in the inhaler and are therefor unsafe.

Bergner et al. make similar observations in the Journal of the American Medical Association (Bergner A et al JAMA, 1993, 269:1506). They reported that exacerbations of asthma occur when patients continue to use medicament dispensing devices beyond the specified number of sprays. They observe that the problem is that patients are unable to tell by sight, sound or taste when the dose is no longer adequate, so they generally continue to use their inhalers until the canister is exhausted. They noted that, ". . . patients should keep a written tally, although this is cumbersome and unlikely to occur." In other writings the same author states that patients generally do not count sprays and are not aware of how close they are to the end of the specified number of sprays, therefore, when their asthma exacerbates, they do not make the association between the exacerbation and the diminishing doses that may be delivered toward the end of the canister's life.

The degree of this problem is multiplied by the magnitude of its scale. According to some authorities, 70 million patients require pharmaceutical metered-dose inhalers worldwide.

SUMMARY OF THE INVENTION

In the present invention, the inhaler adapter incorporates one or more mechanical features that permit a mass balance experiment to be performed by the user using only the adapter itself, the inhalant vessel in question, and possibly a tabletop or other level surface. This mechanism for performing a mass balance experiment is directed at assessing the mass of the aerosol material remaining in the vessel. In particular, the first objective is to assess whether or not the inhaler vessel has been depleted to the design end of life wherein some material may remain in the vessel but not enough material remains to assure proper functioning of the metering system.

Embodiments chosen for illustration include both stable and unstable balance mechanisms. In configurations where the pivot point is fixed and the center of gravity lies above the pivot axis, the mechanism is unstable. Conversely, when the center of gravity is below the pivot axis, the mechanism is stable. The unstable mechanization produces a definitive toggling action at a defined threshold of depletion, whereas the stable balance configuration is used to produce a continuous indication of the depletion state.

In addition to the embodiments that incorporate a defined pivot axis, I have also disclosed an embodiment that utilize a rotational balance mechanism that does not rotate on a defined axis. For example a balance mechanism is effected by incorporation of a curved base surface on which the inhaler is free to rock. When the radius of curvature of such a surface is greater than the height of the center of gravity, the result is a stable balance which is useful in generating a continuous indication of the depletion level of an inhaler which incorporates this mechanism.

BRIEF DESCRIPTION OF THE DRAWINGS

FIG. 1 is an exploded view of an inhaler adapter constructed in accordance with the teachings of the present invention.

FIG. 1A is an assembled view of the inhaler of FIG. 1.

FIG. 2 is an alternative embodiment incorporating a flat base at the cartridge end.

FIG. 3 is an embodiment with a flat base at the mouth end.

DETAILED DESCRIPTION OF THE INVENTION

Figure 4:
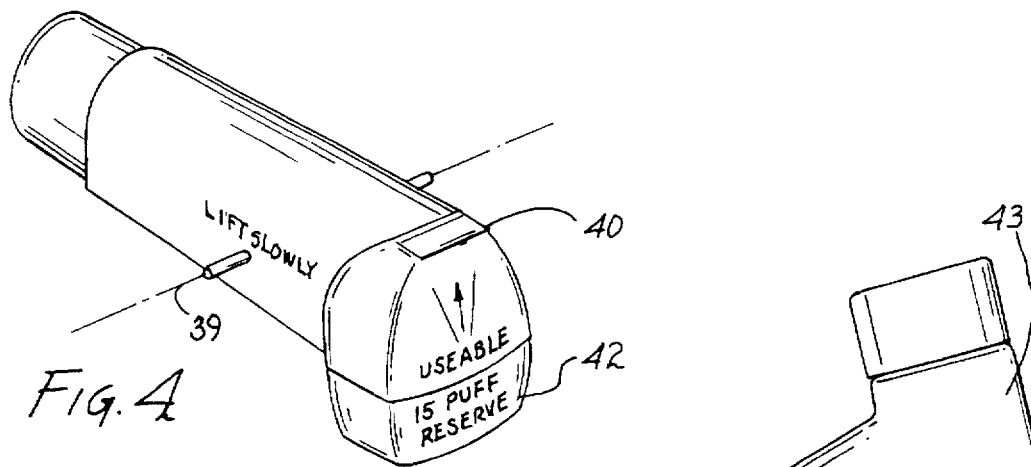
FIG. 4 is an embodiment with a fingertip pivot mechanism.

Referring now to FIGS. 1 and 1A, an unstable embodiment is shown wherein a fulcrum structure 1 is affixed to one side of an inhaler adapter housing 2. A standard commercially available cylindrical cartridge 3 containing medicament is shown inserted into a cavity 9 in the housing 2. A fitted mouthpiece cover 4 is shown in place over the mouthpiece 10 of the inhaler adapter 2. The entire assembly rests on a level surface 5. The mouthpiece cover 4 and the adapter housing 2 are depicted with examples of explanatory legends 6 and 7 which could serve to instruct a user.

In operation the user sets the assembly on a substantially level surface 5 such as a tabletop or counter. In this condition the unit is free to tilt around the pivot axis established as the intersection of the tip of the fulcrum 1 and the level surface 5. The user overtly tilts the assembly so that the cartridge end 12 rests on the level surface 5 possibly by applying downward fingertip pressure on the cartridge 3. Any fluid mass of medicament and liquid propellent within the cartridge 3 will naturally flow to the lowest point in the cartridge which is the cartridge end 12 in contact with the level surface 5. Next, the user releases pressure from the assembly and observes its response. If the mass of the fluid content is sufficient to bias the center of gravity of the assembly to the left of the vertical projection 13 of the fulcrum 1 as shown in FIG. 1, then the assembly will remain in its preset position as shown. If the contained mass is less than this critical amount, then the center of gravity will lie to the right of the vertical projection 13 of the fulcrum causing the unit to tilt so that the mouthpiece end of the adapter falls to the level surface 5. This tilting action provides the user with an accurate, reliable and sharply defined mechanism for recognizing whether the contents of the canister have been depleted to the appropriate end of its useful life.

In performing the experiment thus described, the user may optionally install the mouthpiece cover 4 as shown in FIG. 1 or remove it. Since the mouthpiece cover 4 has a finite mass, the presence of the cover will bias the experiment. This biasing results in a desired feature of the invention. The location of the fulcrum element 1 is precisely located so that when the mouthpiece cover 4 is removed, the balance experiment yields a determination of the cartridge end of life; with the mouthpiece cover 4 installed, the experiment yields a determination of a defined reserve capacity. The amount of the associated reserve capacity is related to the mass of the mouthpiece cover and its projected lever arm.

In FIG. 1, legend 6 is an example of a marking that may be affixed to the mouthpiece cover which provides the user with an indication of the reserve capacity that is associated with the mass of the cover. By affixing such a legend to the mouthpiece cover itself, any possible ambiguity may be precluded in the minds of a user since the legend regarding reserve capacity is automatically removed when the mouthpiece cover is removed. The result is a mechanism that allows performing two distinct and unambiguous experiments. The reserve capacity test offers the user a warning when the cartridge nears its functional depletion point. This capability could be used, for example, to alert the user as to the need to refill a prescription or could be used to advise the user with respect to taking a particular cartridge on an extended outing.

To facilitate low cost manufacturing, a small bias weight 8 could be included almost anywhere on the inhaler housing 2. The bias weight may be used as a calibration technique to more accurately fix the correct mass to be used in the above test; the bias weight could be machined into the body of the adapter to achieve the precise mass thresholding point that is desired. To the extent that the manufacturing process yields significant unit-to-unit balance point variability, then the bias weight 8 could be adjusted on a unit-to-unit basis. In the event the body of the adapter is injection molded, there is not likely to be significant unit-to-unit variation; however, such a bias weight 8 would be useful in developing the mold design. The fulcrum position in the original mold need not be precisely predetermined; instead a molded-in bias weight could be itteratively trimmed after fabrication and testing. Once the bias weight dimension is thus empirically established, the mold could be adjusted in the single dimension of the trim weight feature.

Referring now to FIG. 2, an alternative embodiment is shown wherein the inhaler adapter housing 15 incorporates a flat base feature 16. In operation, the user sets the inhaler 15 on a level surface 17 and releases it. If the inhaler remains standing as illustrated in FIG. 2, then the mass of the material in the canister is greater than the threshold level, otherwise the assembly will topple over in a clockwise direction.

The principle of operation for the second embodiment is the same as that of the first embodiment. In this case, however, the axis of rotation is established by the right edge 18 of the flat base 16. All of the comments regarding the first embodiment apply to the embodiment of FIG. 2.

Referring now to FIG. 3, an embodiment akin to that of FIG. 2, the inhaler housing 28 incorporates a flat base 29. In application, the user sets the assembly on a flat surface 30. If the unit immediately topples over in the counterclockwise direction, the medicament cartridge is not depleted. The edge 31 of the flat base 29 acts as the effective fulcrum in this procedure. As before, the mouthpiece cover 32 can be used as a bias weight so that the procedure can be conducted either with or without the cover. With the mouthpiece cover 32 installed, the procedure yields an indication of reserve capacity in the same manner as previously discussed.

FIG. 4 illustrates yet another embodiment of the invention. Pivot pins 39 protrude from opposite sides of the inhaler housing 40. The pivot pins 39 are intended to be lightly gripped between the user's thumb and forefinger. In operation the user slowly lifts the assembly off of a level surface 41. The assembly is free to rotate in the user's fingertips as it is lifted off the surface. Depending on the longitudinal position of the center of gravity of the assembly relative to the pivot pins, the assembly will either rotate clockwise or counterclockwise. The pivot position is chosen so that when the mouthpiece cover 42 is removed, the threshold between the two rotational directions occurs when the medicament vessel is just at its functional depletion point. As with other embodiments, the contents of the vessel may be assessed with respect to reserve capacity by performing the same test but with the mouthpiece cover 42 in place over the mouthpiece as illustrated in FIG. 4.

The position of the pivot pins 39 may be above or below the center of gravity of the assembly. When the pivot pins are slightly below the center of gravity, the system is unstable which has the desirable effect of accelerating any initial imbalance caused by a longitudinal offset in the center of gravity position. This makes the test sharp and definitive. The pivot point position should not be placed too far below the center of gravity or the test becomes sensitive to inadvertent longitudinal acceleration in the motion of the user's fingers as the assembly is lifted off the level surface 41.

Figure 5:
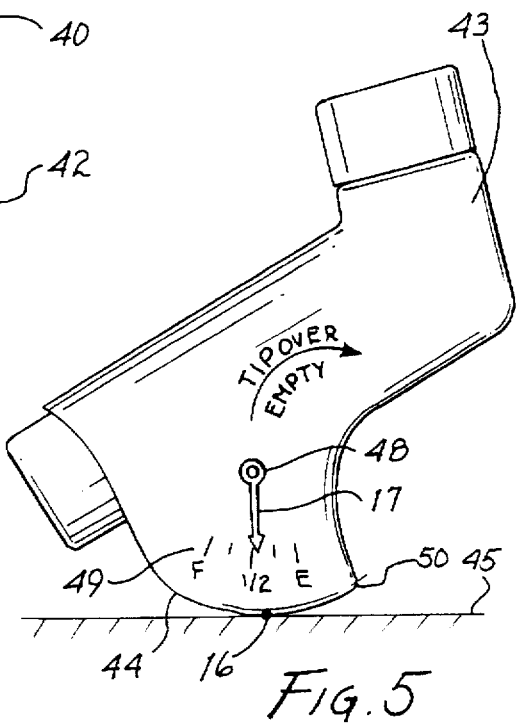
FIGS. 5 and 6 are alternative embodiments of the present invention incorporating a curved base adapter.

FIG. 5 shows an inhaler housing 43 having a curved base 44. This embodiment incorporates both stable and unstable balance features. The stable balance feature offers the ability to assess the continuous mass of the cartridge content. The curved base 44 is free to rock on the level surface 45. The radius of curvature of the curved base 44 is made greater than the height to the center of gravity of the assembly so that the device will be stable in most of its operating range and will naturally move to a resting position such that the center of gravity of the assembly lies directly above the contact point 46 between the curved base 44 and the level surface 45. The angular orientation of the inhaler assembly at steady state will thus be a continuous function of the mass of the material in the canister since the mass in the canister will shift the position of the center of gravity. An indicator needle 47 is suspended from a support point 48. The indicator needle 47 hangs vertically and points to a position on the indicator scale 49 which is a function of the angular orientation of the inhaler assembly. The legends on the indicator scale 49 are analogous to the legends on an automobile gas gauge and are thus familiar and intuitive to the majority of users.

The curved base 44 abruptly terminates at corner point 50. Corner point 50 is the contact point for an inhaler which is at its functional depletion point. At this point the radius of curvature becomes less than the height of the center of gravity and unstable operation results. If the mass in the canister falls below this defined level, then the assembly will not stand in equilibrium on the curved base 44 and instead will topple over in a clockwise direction. The tip over feature of this embodiment provides a precise and definitive indicator of the critical end point in the useful life of the cartridge. The tip-over point might be analogous to the definitive point at which an automobile runs out of gas; this would correspond to the point at which the needle indicator 47 points to the "E" on the indicator scale 49.

Figure 6:
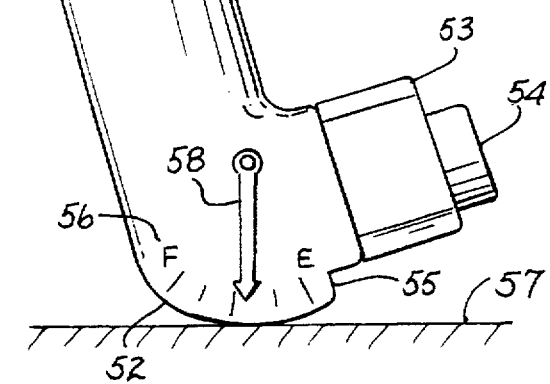

FIG. 6 illustrates an embodiment similar to that of FIG. 5. The inhaler housing 51 incorporates a curved base feature 52. The mouthpiece cover 53 incorporates a counterweight 54. As in the previous embodiment, an indicator needle 58 hangs vertically to point to a reading on the indicator scale 56. The counterweight 54 serves to bias the center of gravity of the assembly to the right sufficiently that the unit will naturally rock on the level surface 57 when the canister contains a usable amount of medicament. The location of the counterweight is not critical; the counterweight may alternatively be incorporated into the structure of the mouthpiece itself. The curved surface 52 has an abrupt termination 55. The abrupt termination 55 serves to provide a tip over feature as discussed in relation to the previous embodiment.

Figure 7:
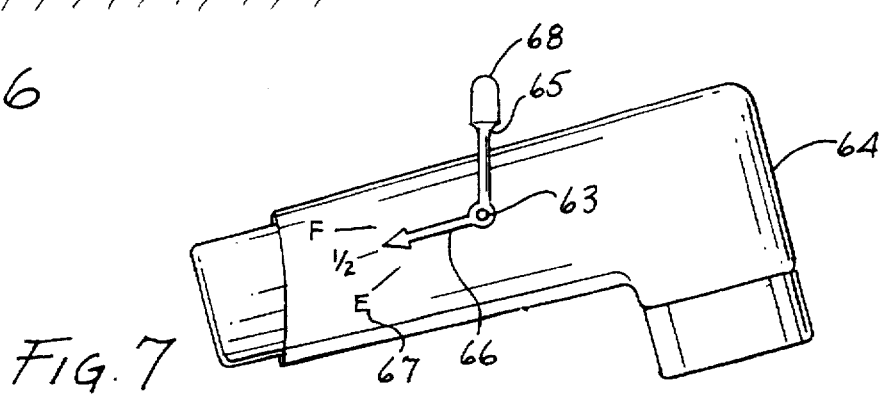
FIG. 7 is an embodiment with finger held suspension mechanism and needle indicator.

FIG. 7 illustrates a stable embodiment of the invention that would not require the use of a tabletop or other level surface. A pair of pivot points 63 are located on opposing sides of the inhaler housing 64. The pivot points 63 are located somewhat above the center of gravity of the assembly. A straddle element 65 straddles the inhaler housing 64 with rotationally free attachments at the pivot points 63. Rigidly affixed to the straddle element 65 is a pointer element 66 which points to a position on an arced indicator scale 67. Symmetrically affixed to the two sides of the straddle element 65 are the ends of a flexible loop 68. Flexible loop 68 could be string for example.

In operation, the user holds the assembly by the flexible loop 68 and reads the dial indication on the indicator scale 67. The center of gravity of the assembly will take a position directly below the pivot points 63. Consequently, the inhaler housing 64 will rotate in response to the change in the longitudinal position of the center of gravity of the assembly as associated with the state of depletion of the inhaler cartridge. The use of the flexible element 68 prevents the user from inadvertently applying torque on the pivot axis which would have the potential of erroneously biasing the measurement indication. One alternative to the flexible element 68 would be a rigid finger grip element attached to the straddle element 65 possibly through a second pivot means.

The principle pivot point 63 is set at such a position that through the full excursion of the measurement range, the cartridge remains angled downward as illustrated in FIG. 7. This assures that the fluid content of the cartridge remains biased against the bottom of the cartridge thus insuring that the measurement is continuous, repeatable and monotonic. This consideration would apply to several of the embodiments described herein.

Figure 10:
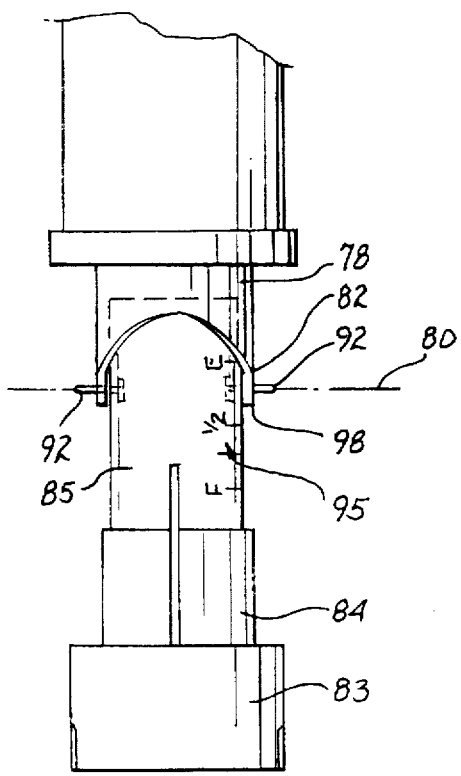
FIG. 10 shows the dispenser of FIG. 8 rotated 90 degrees to reveal the externally extending pivot pins.
Figure 8:
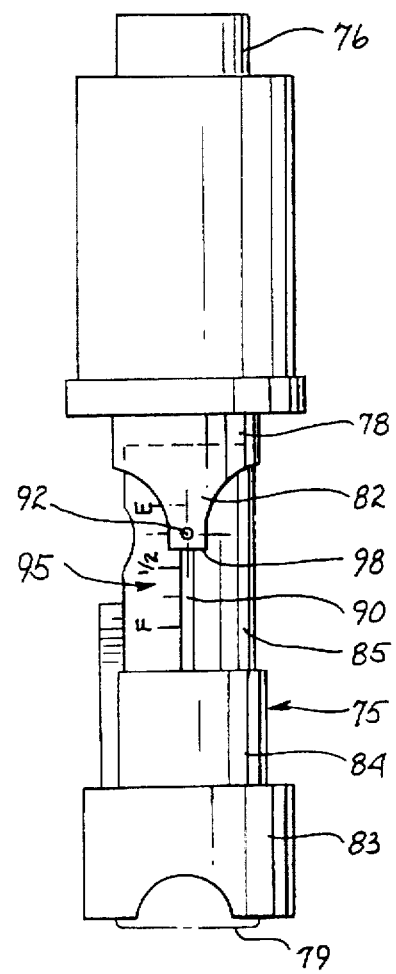
FIG. 8 is a side elevational view of a commercially available articulated aerosol medicament dispenser modified to incorporate the teachings of the present invention.
Figure 9:
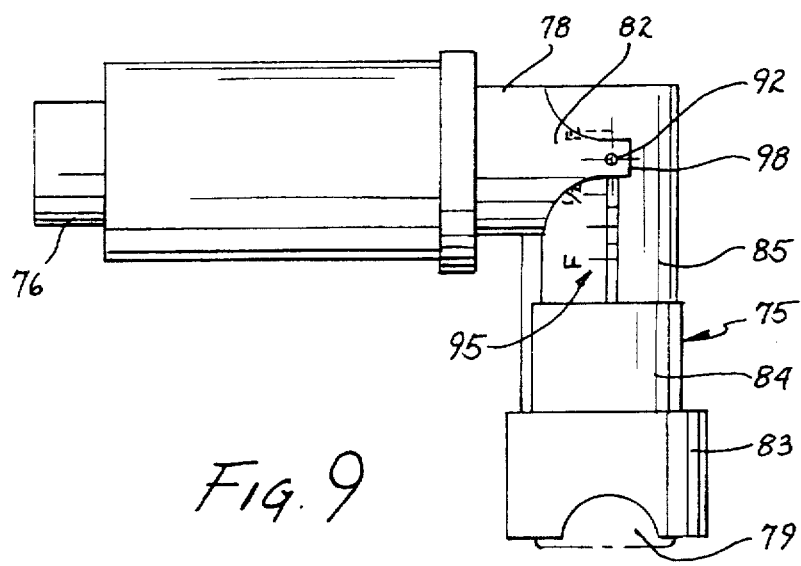
FIG. 9 is a side elevational view of the dispenser of FIG. 8 shown in the articulated position.

Referring now to FIGS. 8, 9 and 10, an embodiment of the present invention is shown implemented in a collapsible or articulated aerosol medicament dispenser of the type presently available on the market. FIG. 8 is a side elevational view of a dispenser incorporating the present invention. FIG. 10 illustrates the dispenser of FIG. 8 rotated 90 degrees showing pivot pins extending therefrom. FIG. 9 illustrates the dispenser in the articulated position for use by the patient. Such dispensers are shown in U.S. Pat. Nos. 3,994,421 and 4,637,528; reference may had to those documents for a complete description of the details of construction. Briefly, the structure includes a hollow cylindrical housing 75 and a cylindrical sleeve 78. The end of the sleeve 78 is provided with a mouthpiece which is covered with a cap 76. An aerosol container 79 is inserted axially into the housing 75 and is frictionally held in position within the housing.

The dispenser parts may be telescopically collapsed for storage but are shown in the extended and articulated positions respectively. When it is desired to use the dispenser, the parts are extended as shown in FIGS. 8 and 10, and the apparatus is then articulated as shown in FIG. 9. It should be noted that the sleeve 78 is pivoted with respect to the housing 75 about an axis 80. In the prior art, this axis was formed by retention "studs" (not shown) that are positioned internally of ears 82 in the sleeve 78.

The housing 75 is formed of a base section 83 and concentrically mounted head sections 84 and 85 respectively. Section 85 is provided with a pair of longitudinally extending slots 90 which extend through its sidewall on opposite sides thereof in parallel relationship. In the prior art, the above mentioned studs are pressed inwardly into the studs so that they snap in place and thereby guide the parts, as they telescope together, by sliding within the slots.

The present invention provides externally extending pivot pins 92 that extend from the studs of the prior art to define the axis of rotation 80, and that may be conveniently held between the thumb and forefinger of the user's hand. A scale 95 is provided on the section 85 adjacent the slots 90; the scale provides a means for determining not only the availability of medicament, but also a measurement thereof. In use, the position of section 85 is adjusted by sliding it into or out of the cylindrical sleeve portion 78 until the entire unit balances when suspended between the forefinger and thumb of the user; the remaining amount or mass of medicament is then indicated on the scale 95 opposite a convenient reference point such as the edge 98 of the ear 82.

The present invention is in essence a measurement system. All real world measurement systems must contend with various types and sources of error; there are usually a large number of mechanisms by which errors can influence a measurement. But usually, there are only a few error mechanisms which can be considered dominant. This is partly the result of the mathematical fact that uncorrelated errors combine as their root mean square; smaller error elements rapidly drop out by virtue of the square law.

In the present invention, it is considered likely that dimensional repeatability will comprise one dominant category of error mechanism when the invention is applied as a low cost, high production rate article. In that regard, one notable dimensional element that falls in this category is the overall length of the cartridge or vessel. The following example of error analysis related to this particular dimensional element is presented for the purpose of illustration.

Six Proventil® brand metered dose inhaler cartridges from three distinct manufacturing lots were examined and measured to obtain an indication of the expected variability of the length of the canisters. Among the six articles measured, the maximum deviation in the length of these vessels was 0.011 inches and the standard deviation was 0.004 inches. It was observed that the dominant variable sub-element in the overall length of the cartridge was the length of the plastic stem that extended from the metal Proventil canister. The effect of the dimensional variability of the cartridge stem is to displace the canister contents with respect to the pivot axis by an amount comparable to the variability of the exposed stem length.

The fundamental principle of the mass balance element of the invention actually relies on torque balancing. In the non-accelerating condition, torque is the integrated product of mass and level arm length. Variation in the effective lever arm will produce an error in mass estimation of like proportion. For example, consider the embodiment of FIG. 4 applied to a standard Proventil® metered dose inhaler cartridge; the lever arm in this case may be about 1.5 inches. So the standard error proportion expected from the variation in the length of the inhaler cartridge is 0.004/1.5 or 0.27%. That corresponds to the mass of about one half of a single puff from the Proventil® cartridge; so this error source would not be problematic.

Another potential error associated with the embodiment of FIG. 4 is the torque disturbance that a user may inadvertently apply through the frictional coupling between her fingertips and the pivot pins. Experimental trials have shown that with the use of a small diameter pin (for example, 0.067 inches), the torque disturbance error is quite small and the mass of a single puff can be reliably discriminated.

Yet another error source to be considered is the error due to the use of a level surface that may not be perfectly level. When the test surface is tilted, the vertical projection of the center of gravity of the inhaler assembly will be horizontally displaced relative to the fixed location of the pivot axis. The amount of this horizontal displacement will be a direct function of the vertical separation between the center of gravity and the pivot axis; the greatest sensitivity to tilt will thus occur in the geometries having the greatest vertical separation. Among the embodiments discussed above, that of FIG. 2 for example, stands to be substantially more sensitive to this error source than that of FIG. 4 which has its pivot axis near its center of gravity.

Clearly the expectation for the magnitude of this "level surfaces" error is related to the expectation as to the tilt in the population of "level surfaces". In an attempt to quantifying the latter, numerous typical surfaces in one particular US home were measured for tilt. The surfaces included the top or "horizontal" surfaces of night stands, bathroom and kitchen counters, desks, bedroom dressers, a TV top, a piano top, etc. These were all surfaces that might reasonably be selected by a user to assess the depletion level of an inhaler by the present invention. Of the 28 surfaces tested, the maximum tilt measured was 10.4 milliradians and the standard deviation of the measurement set was 2.6 milliradians.

This standard deviation value can be treated as an expectation with respect to the likely magnitude of the tilt error. For example, in the geometry of FIG. 2, the vertical separation between the pivot axis and the center of gravity could be about 1.4 inches. The resulting horizontal displacement of the center of gravity given a 2.6 milliradian tilt is then 0.0036 inches. This shift in the effective center of gravity position adds torque on one side of the balance and subtracts torque from the other side; a compensating change in the lever arm length on one side only would need to be twice as great. So the effect is comparable to a lever arm length change on the medicament side of the balance of 0.0072 inches. In the geometry of FIG. 2, the horizontal length of the lever arm between the pivot axis and the medicament is about 1.3 inches. So the effective proportion of error caused by the tilt is 0.0072/1.3=0.55%. For a 200 dose Proventil® inhaler, for example, that would correspond to an expected error at one standard deviation of 1.1 puffs. Thus, even considering a more sensitive geometry as in FIG. 2, the expected error due to test surface tilt is of little significance and is clearly dwarfed by the usual errors in the various methods of the prior art.

What is claimed is:

1. An aerosol medicament dispensing system comprising:
   (a) a pressurized medicament container containing a mass of medicament to be dispensed;
   (b) an adapter for removably supporting said container; and
   (c) means formed integrally with said adapter for permitting rotation of said container and adapter about an axis to provide an indication of the mass of medicament remaining in said container.

2. An aerosol medicament dispensing system comprising:
   (a) a pressurized medicament container containing a mass of medicament to be dispensed;
   (b) an adapter having an open end exposing a cavity to receive and removably support said container, and having a mouthpiece for directing medicament to a user patient; and
   (c) balance means formed integrally with said adapter responsive to the mass of medicament for permitting rotation of said container and adapter about an axis to provide an indication of the mass of medicament remaining in said container.

3. The combination set forth in claim 2 wherein said adapter includes means forming a fulcrum for contacting a horizontal surface to permit rotation thereabout.

4. The combination set forth in claim 3 wherein said fulcrum is positioned intermediate said open end and said mouthpiece.

5. The combination set forth in claim 2 wherein said adapter includes a flat base formed therein and positioned for contacting a horizontal surface to thereby support said adapter and container; said flat base including an edge defining an axis of rotation.

6. The combination set forth in claim 5 wherein said edge is positioned intermediate said open end and said mouthpiece.

7. An aerosol medicament dispensing system comprising:
   (a) a pressurized medicament container containing a mass of medicament to be dispensed;
   (b) an adapter having an open end exposing a cavity to receive and removably support said container, and having a mouthpiece for directing medicament to a user patient;
   (c) balance means formed integrally with said adapter responsive to the mass of medicament for permitting rotation of said container and adapter about an axis to provide an indication of the mass of medicament remaining in said container; and
   (d) a removable mouthpiece cover having a predetermined mass to permit the mouthpiece cover, when in place on the adapter, to counterbalance a portion of the medicament in said container and thereby permit the confirmation of a reserve amount of medicament in said container.

8. An aerosol medicament dispensing system comprising:
   (a) a pressurized medicament container containing a mass of medicament to be dispensed;
   (b) an adapter having an open end exposing a cavity to receive and removably support said container, and having a mouthpiece for directing medicament to a user patient;
   (c) balance means formed integrally with said adapter responsive to the mass of medicament for permitting rotation of said container and adapter about an axis to provide an indication of the mass of medicament remaining in said container; and
   (d) means defining a bias weight positioned on said adapter to permit calibration of the dispensing system's balance.

9. The combination of claim 8 wherein said bias weight is formed integrally with said adapter.

10. An aerosol medicament dispensing system comprising:
    (a) a pressurized medicament container containing a mass of medicament to be dispensed;
    (b) an adapter having an open end exposing a cavity to receive and removably support said container, and having a mouthpiece for directing medicament to a user patient; and
    (c) said adapter including pivot pins extending therefrom defining an axis of rotation and positioned to be gripped by the user patient to permit rotation of the adapter and container thereabout.

11. An aerosol medicament dispensing system comprising:
    (a) a pressurized medicament container containing a mass of medicament to be dispensed;
    (b) an adapter having an open end exposing a cavity to receive and removably support said container, and having a mouthpiece for directing medicament to a user patient; and
    (c) said adapter including a curved base portion formed integrally therewith for contacting a horizontal surface to permit the adapter and container to rock on said surface to a position indicating the mass of medicament remaining in said container.

12. The combination set forth in claim 11 including means defining an indicator supported on said adapter for pivotal movement and positioned above said curved surface when the surface is on said horizontal surface.

13. The combination set forth in claim 12 including a scale positioned adjacent said indicator, said indicator and scale providing an indication of the mass of medicament remaining in said container.

14. An aerosol medicament dispensing system comprising:
    (a) a pressurized medicament container containing a mass of medicament to be dispensed;
    (b) an adapter having an open end exposing a cavity to receive and removably support said container, and having a mouthpiece for directing medicament to a user patient; and
    (c) said adapter including a pair of pivot points defining an axis of rotation, lifting means pivotally attached to said pivot points to permit a user to lift the adapter and container, a pointer secured to said lifting means, and a scale positioned adjacent said pointer to provide an indication of the mass of medicament remaining in said container once an adapter and container are raised.

15. An aerosol medicament dispensing system comprising:
    (a) a pressurized medicament container containing a mass of medicament to be dispensed;

(b) an adapter including a housing having an open end exposing a cavity to receive and removably support said container;

(c) said adapter also including a sleeve slidably and pivotally attached to said housing to permit said housing and sleeve to telescope and pivot with respect to each other;

(d) said housing including an extension having slots therein, said extension slidable into said sleeve to permit telescoping movement;

(e) means defining external pivot pins attached to said sleeve, said pivot pins defining a pivot axis that is slidable along said slots.

16. The combination set forth in claim 15 wherein said housing and sleeve pivot about said axis with respect to each other.

17. The combination of claim 15 including a scale positioned adjacent said slot to provide an indication of the mass of medicament remaining in said container.

* * * * *